United States Patent
Verrior et al.

(10) Patent No.: US 6,200,303 B1
(45) Date of Patent: *Mar. 13, 2001

(54) METHOD AND KIT FOR TRANSVENOUSLY ACCESSING THE PERICARDIAL SPACE VIA THE RIGHT ATRIUM

(75) Inventors: Richard L. Verrior, Wellesley Hills; Sergio Waxman, Brighton, both of MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/296,285

(22) Filed: Apr. 22, 1999

Related U.S. Application Data

(63) Continuation-in-part of application No. 08/841,344, filed on Apr. 30, 1997, now Pat. No. 5,968,010.

(51) Int. Cl.[7] .................................................. A61M 31/00
(52) U.S. Cl. ............................................ 604/508; 604/500
(58) Field of Search ............................. 604/48, 500, 506, 604/507, 508, 509, 510, 513, 164.02–164.09, 164.1, 164.11, 171, 173, 181, 170.01, 170.02, 170.03

(56) References Cited

U.S. PATENT DOCUMENTS

| | | | |
|---|---|---|---|
| 3,630,207 | 12/1971 | Kahn et al. | 128/350 R |
| 3,680,544 | 8/1972 | Shinnick et al. | 128/2 R |
| 4,003,379 | 1/1977 | Ellinwood, Jr. | 128/260 |

(List continued on next page.)

FOREIGN PATENT DOCUMENTS

WO 98/48881   11/1998   (WO) .

OTHER PUBLICATIONS

International Search Report for PCT Appl. No. PCT/US00/07444, 5 pages, mailed Jul. 12, 2000.

Avitall, B. et al., "A New Technique For AV Nodal Modification Using Perinodal Injection Of A Sclerosing Agent", *JACC,* vol. 17, No. 2, Feb., 1991, pg. 174A. (Abstract only).

Avitall, B. et al., "Iontophoretic of Procainamide and D–Sotalol Into Arrhythmogenic Myocardium: Efficacy in Vertricular Tachycardia Suppression", *JACC,* vol. 17, No. 2, Feb., 1991, pg. 39A. (Abstract only).

(List continued on next page.)

*Primary Examiner*—Manuel Mendez
(74) *Attorney, Agent, or Firm*—Sterne, Kessler, Goldstein & Fox P.L.L.C.

(57) ABSTRACT

A method and kit for accessing the pericardial space take advantage of the fact that the right auricle is a thin-walled, low-pressure structure which can be readily penetrated without damaging the pericardium or the epicardium. The method includes the step of passing a guide catheter through a selected peripheral vein to establish a transvenous route to the right auricle of the heart. An infusion guide wire and a leading guide wire are passed through the guide catheter and into the right auricle so that a distal end of the leading guide wire is positioned against a wall of the right auricle. The leading guide wire is located within a lumen of the infusion guide wire and protrudes outward, preferably about 2 mm, from a distal end of the infusion guide wire. The wall of the right auricle is then pierced with the distal end of the leading guide wire. After the wall of the right auricle is pierced, at least one of the infusion guide wire and the leading guide wire are advanced into the pericardial space. Once in position, the infusion guide wire and/or the leading guide wire can be used as a conduit over which a desired catheter may be introduced for performing a specific medical procedure. Alternatively, the infusion guide wire and/or the leading guide wire can be used to perform a specific medical procedure without the introduction of an additional device into the pericardial space.

29 Claims, 9 Drawing Sheets

U.S. PATENT DOCUMENTS

| | | | |
|---|---|---|---|
| 4,146,029 | 3/1979 | Ellinwood, Jr. | 128/260 |
| 4,173,981 | 11/1979 | Mortensen | 128/348 |
| 4,181,123 | 1/1980 | Crosby | 128/6 |
| 4,256,115 | 3/1981 | Bilitch | 128/419 P |
| 4,292,976 | 10/1981 | Banka | 128/656 |
| 4,296,100 | 10/1981 | Franco | 424/108 |
| 4,319,562 | 3/1982 | Crosby | 128/1 R |
| 4,567,900 | 2/1986 | Moore | 128/784 |
| 4,619,247 | 10/1986 | Inoue et al. | 128/6 |
| 4,699,147 | 10/1987 | Chilson et al. | 128/642 |
| 4,708,145 | 11/1987 | Tacker, Jr. et al. | 128/419 D |
| 4,717,387 | 1/1988 | Inoue et al. | 604/264 |
| 4,765,341 | 8/1988 | Mower et al. | 128/785 |
| 4,769,016 | 9/1988 | Labianca | 604/280 |
| 4,865,037 | 9/1989 | Chin et al. | 128/419 D |
| 4,884,567 | 12/1989 | Elliott et al. | 128/303 R |
| 4,946,457 | 8/1990 | Elliott | 606/1 |
| 4,961,731 | 10/1990 | Bodicky et al. | 604/264 |
| 4,991,578 | 2/1991 | Cohen | 128/419 D |
| 4,991,603 | 2/1991 | Cohen et al. | 128/786 |
| 4,998,975 | 3/1991 | Cohen et al. | 128/419 D |
| 5,033,477 | 7/1991 | Chin et al. | 128/785 |
| 5,092,848 | 3/1992 | deCiutiis | 604/170 |
| 5,137,510 | 8/1992 | VanDeripe | 604/28 |
| 5,147,336 | 9/1992 | Wendell et al. | 604/283 |
| 5,269,326 | 12/1993 | Verrier | 128/642 |
| 5,354,279 * | 10/1994 | Hofling | 604/164 |
| 5,554,114 | 9/1996 | Wallace et al. | 604/53 |
| 5,569,197 | 10/1996 | Helmus et al. | 604/96 |
| 5,713,849 | 2/1998 | Bosma et al. | 604/28 |
| 5,722,972 | 3/1998 | Power et al. | 606/7 |
| 5,725,512 | 3/1998 | Swartz et al. | 604/280 |
| 5,968,010 * | 10/1999 | Waxman et al. | 604/49 |

OTHER PUBLICATIONS

Avitall, B. et al., "Iontophoretic Delivery of Dobutamine: An Effective Method To Increase Contractility of Non–Transmural Infarcts", *JACC*, vol. 17, No. 2, Feb., 1991, pg. 27A. (Abstract only).

Baim et al., *Cardiac Catherization, Angiography, and Intervention*, Fifth Edition, Williams and Wilkins Publishing, 1996, pp. 809–811 and 813.

Brockenbrough et al., "A New Technique for Left Ventricular Angiocardiography and Transseptal Left Heart Catheterization," *The American Journal of Cardiology*, Dec., 1960, pp. 1062–1064.

Buselmeier, T.J. et al., "Treatment of Intractable Uremic Pericardial Effusion: Avoidance of Pericardiectomy With Local Steroid Instillation", *Journal of the American Medical Association*, vol. 240, No. 13, 1978, pp. 1358–1359.

DiCarlo, S.E. et al., "Exercise training enhances cardiac afferent inhibition of baroreflex function", *The American Physiological Society*, Order No. 0363–6135, 1990, pp. H212–H220.

Dorward, P.K. et al., "Blockade Of Cardiac Nerves By Intrapericardial Local Anaesthetics In The Conscious Rabbit", *Aust. J. Exp. Biol. Med. Sci.*, vol. 61, (Pt. 2), 1983, pp. 219–230.

Miyazaki, T. et al., "Prostaglandins in the Pericardial Fluid Modulate Neural Regulation of Cardiac Electrophysiological Properties", *Circulation Research*, vol. 66, No. 1, Jan., 1990, pp. 163–175.

Miyazaki, T. et al., "Presynaptic Modulation of Efferent Sympathetic and Vagal Neurotransmission in the Canine Heart by Hypoxia, High $K^{30,}$ Low pH, and Adenosine", *Circulation Research*, vol. 66, No. 2, Feb. 1990, pp. 289–301.

Uchida et al., "Angiogenic Therapy of Acute Myocardial Infarction by Intrapericardial Injection of Basic Fibroblast Growth Factor and Heparin Sulfate: An Experimental Study," *American Heart Journal*, vol. 130, No. 6, Dec., 1995, pp. 1182–1188.

Verrier, R.L. et al., "Protective zone and the determination of vulnerability to ventricular fibrillation", *The American Physiology Society*, 1978, Order No. 0363–6135/78/0000–0000, pp. H592–H596.

Verrier, R.L. et al., "Prevention Of Ventricular Fibrillation By Use Of Low–Intensity Electrical Stimuli", Reprinted from *the Annals of the New York Academy of Sciences*, 1982, pp. 355–370.

Welt et al., "Second International Symposium on Cardiovascular Drug Delivery," *Circulation*, vol. 95, No. 4, Feb. 18, 1997, pp. 773–776.

Verrier, R. L. et al., "Transatrial Access to the Normal Pericardial Space—A Novel Approach for Diagnostic Sampling, Pericardiocentesis, and Therapeutic Interventions," Circulation: Journal of American Heart Association, on or about Dec. 8, 1998 (based on information presently available), pp. 2331–2333.

* cited by examiner

202

```
┌─────────────────────────────────────────┐
│ SELECT A PERIPHERAL VEIN AS AN ACCESS SITE │──302
└─────────────────────────────────────────┘
                    │
                    ▼
┌─────────────────────────────────────────────────┐
│ PLACE AN INTRODUCER SHEATH IN SAID VEIN TO      │
│ PROTECT THE PERIPHERAL VEIN AND FACILITATE      │──304
│ INTRODUCTION OF VARIOUS CATHETERS               │
└─────────────────────────────────────────────────┘
                    │
                    ▼
┌─────────────────────────────────────────────────┐
│ USE A GUIDE CATHETER TO ESTABLISH A TRANSVENOUS │──306
│ ROUTE TO THE RIGHT AURICLE OF THE HEART         │
└─────────────────────────────────────────────────┘
                    │
                    ▼
┌─────────────────────────────────────────────────┐
│ PASS A NEEDLE CATHETER THROUGH THE GUIDE CATHETER│
│ AND INTO THE RIGHT AURICLE SO THAT A DISTAL END OF│──308
│ THE NEEDLE CATHETER IS AGAINST THE WALL OF THE RIGHT│
│ AURICLE                                          │
└─────────────────────────────────────────────────┘
                    │
                    ▼
┌─────────────────────────────────────────────────┐
│ PIERCE THE WALL OF THE RIGHT AURICLE WITH       │──310
│ THE NEEDLE CATHETER                             │
└─────────────────────────────────────────────────┘
                    │
                    ▼
┌─────────────────────────────────────────────────┐
│ ADVANCE A GUIDE WIRE THROUGH THE NEEDLE CATHETER│──312
│ AND INTO THE PERICARDIAL SPACE                  │
└─────────────────────────────────────────────────┘
                    │
                    ▼
┌─────────────────────────────────────────────────┐
│ USE FLUOROSCOPIC IMAGING TO CONFIRM POSITIONING OF│──314
│ THE GUIDE WIRE WITHIN THE PERICARDIAL SPACE     │
└─────────────────────────────────────────────────┘
```

FIG. 3

METHOD AND KIT FOR TRANSVENOUSLY ACCESSING THE PERICARDIAL SPACE VIA THE RIGHT ATRIUM

CROSS-REFERENCE TO RELATED APPLICATIONS

This application is a continuation-in-part of commonly-owned, U.S. patent application Ser. No. 08/841,344, now U.S. Pat. No. 5,968,010, filed Apr. 30, 1997, entitled "Method for Transvenously Accessing the Pericardial Space via the Right Atrium," which is incorporated herein by reference.

BACKGROUND OF THE INVENTION

1. Field of the Invention

The invention relates to the field of cardiology. More specifically, the invention relates to a method and kit for diagnosing and treating the heart by facilitating access to the pericardial space.

2. Background Art

An important problem in cardiology is the provision of a safe method and kit for diagnosing and treating the heart selectively and without thoracotomy (open chest surgery). Diagnosis or treatment may be pharmacologic or electrophysiologic. For example, in order to deliver electrical stimuli directly to the heart for the purpose of cardioversion or defibrillation, patients often undergo a thoracotomy under general anesthesia for attachment of a "patch" electrode to the epicardial surface. This procedure requires an extensive incision of the pericardium. The "patch" electrode provides a large electrode surface area in contact with the heart so that a sufficient mass of cardiac tissue may be depolarized. Thoracotomy creates the additional complication of wound healing.

It is desirable to provide a method and kit for placing the defibrillation/cardioversion electrodes in contact with the heart muscle without thoracotomy. U.S. Pat. Nos. 4,181,562 and 4,319,562 to Crosby, and U.S. Pat. No. 5,033,477 to Chin et al. disclose methods for placing electrodes in contact with the heart muscles from within the pericardial space without the need for thoracotomy. Access to the pericardial space is gained via a sub-xiphoid route. This involves penetrating the chest wall below the xiphoid process.

The sub-xiphoid route has several disadvantages. First, because the pericardial sac which surrounds the heart is a tight-fitting fibrous membrane, the pericardial space is so small that it is difficult to penetrate the sac without also puncturing, and thereby, damaging the heart itself. Second, accessing the heart via the sub-xiphoid route entails a high risk of infection. These are likely to account for its failure to be adopted into common clinical practice.

In fact, the sub-xiphoid route is presently used almost solely for pericardiocentesis, a process for the aspiration of excess fluid from the pericardial sac. Pericardiocentesis is normally performed to treat cardiac tamponade, a buildup of excess fluid in the pericardial sac. The excess fluid distends the pericardial sac away from the heart such that the risk of puncturing the heart is reduced, but the risk of infection remains high.

U.S. Pat. No. 4,884,567 to Elliott et al., U.S. Pat. No. 4,946,457 to Elliott, and U.S. Pat. No. 4,998,975 to Cohen et al. disclose methods for transvenous implantation of electrodes into the pericardial space. A catheter is introduced through a vein to the atrium where the lateral atrial wall is penetrated in order to introduce electrodes into the pericardial space. A major problem encountered by these methods is how to penetrate the lateral atrial wall without also puncturing the tight-fitting pericardium.

The methods of these patents attempt to solve this problem through several elaborate schemes. One scheme involves using complex catheters to attach to the lateral atrial wall and to pull it back away from the pericardium prior to penetrating the wall in order to avoid puncturing the pericardium. Another approach involves injecting a fluid into the pericardial space to distend the pericardium away from the lateral atrial wall prior to penetrating the wall.

U.S. Pat. No. 4,991,578 to Cohen discloses a method for implanting epicardial defibrillation electrodes into the pericardial space. The method involves entering the pericardial space via the sub-xiphoid route. As discussed above, it is difficult to penetrate the pericardial sac via the sub-xiphoid route without also puncturing, and thereby damaging, the heart itself. Like the method discussed directly above, the '578 patent discloses injecting a fluid into the pericardial space or attaching and pulling on a catheter to distend the pericardial sac away from the heart.

Because each of these known methods is intrinsically cumbersome and hazardous, they have not gained widespread use. What is needed is a simpler, safer, and more effective way of accessing the pericardial space for delivery of electricity directly to the heart muscle.

In addition to providing a convenient location for placement of electrodes, the confines of the pericardial sac provide an excellent opportunity to isolate the heart for treatment and diagnosis. By introducing pharmacologic agents directly into the pericardial sac, high cardiac drug concentrations can be achieved without spillage or systemic distribution to other organs or tissues.

The pericardial sac has been used for containment of pharmacologic agents for a number of years in experimental settings, but delivery has heretofore required open chest surgery to access the pericardial space. U.S. Pat. Nos. 4,003,379 and 4,146,029 to Ellinwood disclose an implantable medication dispensing apparatus which is adapted to dispense drugs to the pericardial sac over a long period of time, for example, to prevent arrhythmias. The Ellinwood patents, however, do not teach a method for routing the drugs into the pericardial sac.

U.S. Pat. No. 5,269,326 to Richard L. Verrier discloses a method for transvenously accessing the pericardial space via the right auricle. The full text of the Verrier '326 patent is incorporated herein by reference as if reproduced in full below. The transvenous method described by Verrier overcomes the limitations noted above with prior methods by providing a method for safely and reliably introducing a catheter and/or electrodes into the pericardial space. Each of the following embodiments of the present invention improve upon the Verrier '326 patent by providing a specific method for exploiting the route discovered by Verrier.

SUMMARY OF THE INVENTION

The disclosed methods and kits for accessing the pericardial space take advantage of the fact that the right auricle is a thin-walled, low-pressure structure which can be readily penetrated without damaging the pericardium or the epicardium. A guide catheter is passed through a selected peripheral vein to establish a transvenous route to the right auricle of the heart.

In one embodiment, an infusion guide wire and a leading guide wire are passed through the guide catheter and into the right auricle so that a distal end of the leading guide wire is positioned against a wall of the right auricle. The leading guide wire is located within a lumen of the infusion guide wire and preferably protrudes outward from a distal end of the infusion guide wire.

The wall of the right auricle is then pierced with the distal end of the leading guide wire. This is preferably accomplished by simultaneously applying an axial force to a proximal end of the infusion guide wire and a portion of the leading guide wire that extends from the proximal end of the infusion guide wire until the distal end of the leading guide wire pierces the wall of the right auricle. It is noted that this can be successfully performed without attaching/fixing a distal end of the guide catheter to the wall of the right auricle. Alternatively, although not preferably, if the leading guide wire does not protrude from the distal end of the infusion guide wire, then the wall of the right auricle can be pierced by the distal end of the infusion guide wire.

After the wall of the right auricle is pierced, the infusion guide wire and/or the leading guide wire can be advanced into the pericardial space. Once in position, the infusion guide wire and/or the leading guide wire can be used as a conduit over which a desired catheter may be introduced for performing a specific medical procedure.

To place the guide catheter in position, a peripheral vein such as one of the femoral veins is selected. An introducer sheath is then placed into the selected vein to protect the entry site. The guide catheter is introduced into the vein through the sheath and is guided downstream through the vein to one of the venae cavae, through the one venae cavae to the right atrium, and through the right atrium into the right auricle. If the jugular vein is selected for access, then the superior vena cava is employed as a route to the right atrium.

The guide catheter is advanced into the apex of the right auricle so that a distal end of the guide catheter is placed against the wall of the right auricle. Fluoroscopic or echocardiographic imaging can be used to visually follow the progress of the guide catheter into the right auricle. Proper placement of the guide catheter against the wall of the right auricle is confirmed when the distal end of the guide catheter moves with the beating of the heart.

Fluoroscopic or echocardiographic imaging can also be used to visually follow the progress of the infusion guide wire and/or the leading guide wire into the pericardial space. Proper placement of the infusion guide wire and/or leading guide wire in the pericardial space can be confirmed when a distal portion of the infusion guide wire and/or leading guide wire begins to take the shape of the contour of the heart.

In a preferred embodiment, the infusion guide wire and the leading guide wire are simultaneously advanced into the pericardial space. Once the pair of guide wires is in position within the pericardial space, the leading guide wire may be removed. Thereafter, the lumen of the infusion catheter can be used to deliver a substance to or remove a substance from the pericardial space.

Additionally, the infusion guide wire and/or the leading guide wire may also act as an electrode for sensing or delivering an electrical signal. One of the guide wires may also embody a fiber optic device or other instrument.

Alternatively, any number of different procedure-specific catheters may be introduced to the pericardial space by passing them over the infusion guide wire and/or the leading guide wire (i.e., the lumen of the procedure-specific catheter is threaded over one or both guide wires). Once a specific catheter is positioned within the pericardial space, a medical procedure may be performed on the heart. Such medical procedures include, for example, the delivery of an electrical signal for pacing, cardioverting and/or ablating arrhythmias; the sensing of an electrocardiogram (ECG) signal; the acute or chronic delivery of a pharmacologic agent; the delivery of a dye or imaging agent; the withdrawal of a fluid sample for analysis; and the withdrawal of fluid for treatment of cardiac tamponade; the imaging/inspecting of heart muscles and coronary arteries for detection of damage and disease; the mapping of electrophysical properties of the heart including excitation and repolarization; and the performing of a surgical procedure.

In another embodiment of the invention, the guide catheter includes means for monitoring blood pressure and electrocardiogram. These features permit placement of the guide catheter into position in the right atrium using electrical and/or hemodynamic indices.

An advantage of the invention is that successful placement of at least one of the infusion guide wire and the leading guide wire into the pericardial space can be confirmed without the need to inject a radiopaque dye. In addition, the guide wires can be used to maintain a stable point of entry into the pericardial space to permit repeated successive introduction of different intrapericardial catheters.

Another advantage of the invention is that the availability of steerable guide wires permit accurate positioning of an intrapericardial catheter at any location within the pericardial space.

A further advantage is that the invention combines off-the-shelf catheters and guide wires to perform certain preferred embodiments of the present invention.

The foregoing and other features and advantages of the invention will be apparent from the following more particular description of preferred embodiments of the invention, as illustrated in the accompanying drawings.

BRIEF DESCRIPTION OF THE DRAWINGS

FIG. 3 is a flow chart showing a method of the invention for introducing a guide wire into the pericardial space via a transvenous route, according to an embodiment of the present invention.

DESCRIPTION OF THE PREFERRED EMBODIMENTS

The preferred embodiments of the invention are discussed with reference to the figures in which like reference numbers indicate like elements. Furthermore, the left most digit of each reference number indicates the number of the figure in which the number first appears. While specific part numbers and configurations are discussed, it should be understood that this is done for illustration purposes only. A person skilled in the art will recognize that other components and configurations may be used without departing from the spirit and scope of the invention.

The invention relates to methods and kits for treating and diagnosing the heart selectively via the pericardial space without surgical trauma or the risks of general anesthesia and infection. Neither thoracic nor sub-xiphoid access is utilized, and there is minimal risk of damage to the pericardium or the epicardium. The methods and kits take advantage of the fact that the pericardial sac isolates the heart such that it may be treated or diagnosed separately from the remainder of the body. Because of its feasibility and safety, these methods and kits could lead to common usage by cardiologists and open up the field of pericardial therapy. Heretofore there has been reluctance to pursue this field because of the hazardous and cumbersome nature of existing techniques for accessing the pericardial space.

Figure 1:
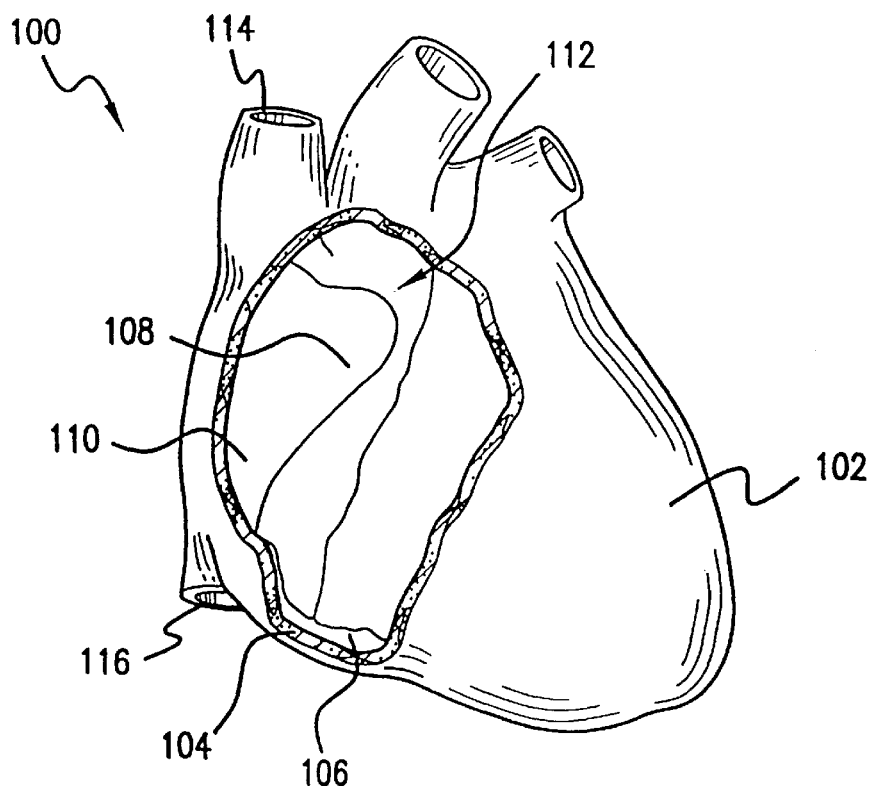
FIG. 1 is a simplified diagram of a human heart with a portion of pericardium 102 cut away.

FIG. 1 shows a heart 100 isolated from the body. Blood is returned to the heart by the superior vena cava 114 and the inferior vena cava 116. The pericardium or pericardial sac 102 encases the cardiac muscle (i.e., epicardium, myocardium and endocardium). A portion of pericardium 102 has been removed to show the underlying cardiac muscle including the right atrium 110. The cut edge of pericardium 102 is designated 104. The small space which is present between the heart muscle and pericardium 102 is known as the pericardial space 106.

In the above referenced U.S. Pat. No. 5,269,326 to Richard L. Verrier, Verrier teaches that the right atrial appendage or right auricle 108 is an ideal site for entry into the pericardial space. A transvenously guided catheter can be made to penetrate the thin wall of right auricle 108 at its apex 112. Verrier teaches accessing the right auricle 108 via conventional venae cavae routes. The present invention improves upon the method taught by Verrier in the '326 patent and provides specific methods that can be used to exploit the route discovered by Verrier. Further, the present invention provides improved methods and kits for penetrating the thin wall of right auricle 108.

Figure 2:
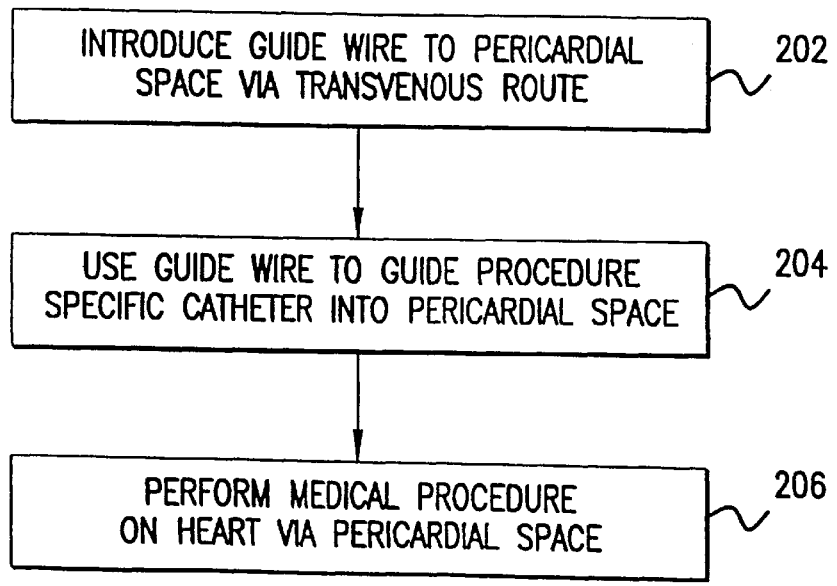
FIG. 2 is a flow chart showing a high level depiction of the present invention.

FIG. 2 is a high level flow chart illustrating the steps of gaining access to the pericardial space to perform a medical procedure. In a step 202, at least one guide wire is introduced into the pericardial space via a transvenous route. In step 204, the guide wire(s) is used to guide a procedure specific catheter into the pericardial space. This is typically done by threading a catheter with a hollow lumen over the guide wire(s) so that the guide wire(s) passes through the lumen of the catheter as it is maneuvered into position. The procedure specific catheter may be, for example, a catheter specifically configured to sense electrical energy (an electrocardiogram) from the epicardium, to deliver electrical energy to the heart for pacing or ablating or cardioverting arrhythmias, to acutely or chronically deliver a pharmacologic agent or other substance to the pericardial space, or to remove fluid from the pericardial space. Alternatively, a guide wire that is used to gain access to the pericardial space can itself be used to perform a specific procedure. Accordingly, it may not be necessary to guide any other device into the pericardial space.

Finally, in a step 206, the medical procedure is performed on the heart via the pericardial space. Any number of procedures may be performed on the heart once the guide wire(s) is in place. In addition, catheters may easily be swapped in and out with little risk to the patient. Thus, an important part of the invention is the method for positioning the guide wire(s) into the pericardial space via the transvenous route.

In an embodiment of the invention, at least one guide wire is left in place during the medical procedure. Thus, if a different catheter is subsequently required, it may be threaded over the guide wire(s) and into the pericardial space. In an alternate embodiment of the invention, the guide wire(s) may be removed after the procedure specific catheter is put in place.

If subsequent introduction of other catheters is desired, a guide wire may be put back into position in the pericardial space by passing it back through the lumen of the procedure specific catheter before the procedure specific catheter is removed. Alternatively, a guide wire may be put back in position in the pericardial space after the procedure specific catheter is removed.

Figure 4:
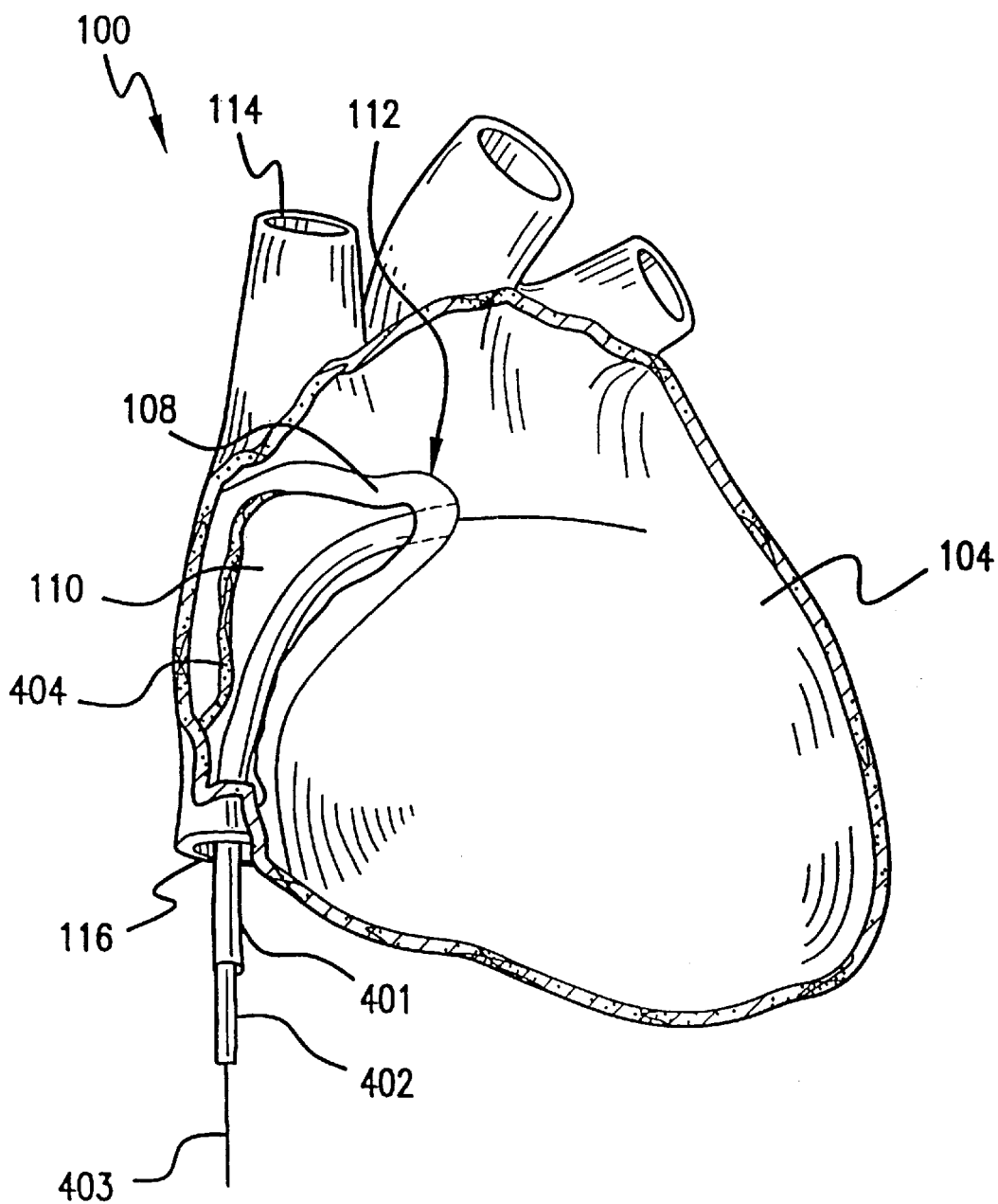
FIG. 4, which is used to explain the method of FIG. 3, is a simplified diagram of a human heart as shown in FIG. 1 but with a portion of the right atrium cut away to show the introduction of catheters into the right auricle.

For a first embodiment, step 202 of positioning the guide wire in the pericardial space is shown in greater detail with reference to FIGS. 3 and 4. FIG. 3 illustrates the steps of the method. FIG. 4 shows the heart 100 of FIG. 1 with a cutaway 404 to illustrate passage of various catheters 401–403 through inferior vena cava 116, through right atrium 110 and into right auricle 108 as described with reference to FIG. 3.

In a step 302, a peripheral vein is selected as an access site. The Verrier '326 patent teaches a variety of peripheral veins that can be used. For example, if a femoral route is chosen, the great saphenous vein, superficial femoral vein or deep femoral vein can be used. Each of these veins leads downstream to the external iliac vein and finally to the inferior vena cava. If a jugular route is chosen, then access to the right atrium will be made through the superior vena cava.

In a step 304, the access site is prepared by placing an introducer sheath into the vein. The introducer sheath will protect the entry site and facilitate entry into the vein. The sheath is preferably a self-sealing sheath that will prevent bleeding. Such sheaths are commercially available and are commonly used for angioplasty and angiography procedures.

In a step 306, a guide catheter 401 is passed through the introducer sheath, through the peripheral vein, through any downstream veins and into one of the venae cavae. From the selected one of the venae cavae, the catheter is passed into the right atrium and into the right auricle. Using fluoroscopic or echocardiographic guidance, the distal tip of guide catheter 401 is placed against the wall of right auricle 108 at apex 112. Proper placement of guide catheter 401 against the wall of the right auricle is then confirmed when the distal end of guide catheter 401 moves with the beating of the heart. In the case of a femoral route, for example, guide catheter 401 may be introduced into one of the femoral veins and then passed through the external iliac vein, through inferior vena cava 116 and into right atrium 110.

In this embodiment, a 7French, multipurpose catheter, available from Cordis Corporation, Miami Lakes, Fla., has typically been employed for guide catheter 401. However, larger or smaller catheters can be selected to accommodate the devices to be introduced therethrough. In an alternate embodiment of the invention, guide catheter 401 may include means for monitoring blood pressure and electrocardiogram. These features permit placement of the guide catheter into position in the right atrium using electrical and/or hemodynamic indices.

In a step 308, a needle catheter 402 is passed through a lumen of guide catheter 401. Needle catheter 402 is advanced through guide catheter 401 until the distal end of needle catheter 402 extends out from the distal end of guide catheter 401. The distal end of needle catheter 402 may then be urged against the wall of right auricle 108 by placing a slight force on the proximal end of needle catheter 402.

In the animal experiments discussed below, the inventors implemented needle catheter 402 by cutting 4 mm from the distal tip of a 23 gauge needle. This 4 mm portion of the 23 gauge needle was then inserted 2 mm into the end of a 3French transit catheter so that 2 mm of the distal tip of the needle extended out from the distal end of the transit catheter. A snug fit of the needle into the lumen of the transit catheter was achieved. In an alternate embodiment, needle catheter 402 may be implemented using any catheter, needle or wire that has a hollow lumen and can be used to pierce the wall of right auricle 108. For example, needle catheter 108 may be implemented using a long Brockenbrough-type needle, available from U.S. Catheter Instrument Company (USCI), Billerica, Mass.

In a step 310, the distal end of needle catheter 402 is used to pierce the wall of right auricle 108 to gain access to the pericardial space. In the preferred embodiment, this is accomplished by simply holding the distal end of needle catheter 402 in contact with the atrial wall at apex 112. As the heart contracts, the atrial wall will be further urged against the sharp tip of needle catheter 402. After a short period of time has elapsed (e.g., 30 to 60 seconds), needle catheter 402 will pierce through the wall of right auricle 108 as a result of the mechanical motion of the heart while it beats. This method is preferred to any method that involves piercing the wall by simply applying a force to the proximate end of needle catheter 402. Any method that forces needle catheter 402 through the atrial wall by applying a large pushing force may have a higher risk that the catheter may go through the wall and damage other heart tissue or even a coronary vessel within the pericardial space. The inventors believe that the risk of damage to the heart is greatly reduced if the natural movement of the heart is allowed to cause the penetration.

In a step 312, a guide wire 403 is advanced through the lumen of needle catheter 402 and into the pericardial space. As guide wire 403 is being pushed into the pericardial space, fluoroscopic or echocardiographic imaging can be used to confirm, as shown in step 314, that guide wire 403 is actually being advanced into the pericardial space as it exits the distal end of needle catheter 402. For example, as guide wire 403 is pushed two to three inches into the pericardial space, it will begin to take the shape of the space that it is being pushed into. When guide wire 403 begins to take the shape of the contour of the heart, the clinician will note this in the fluoroscopic or echocardiographic image. In the preferred embodiment, guide wire 403 is a 0.014 inch, Wizdom guide wire, available from Cordis Corporation.

Once guide wire 403 is in position within the pericardial space, the needle catheter may be removed. Thereafter, any number of different procedure-specific catheters (including surgical instruments such as fiber optic imaging devices) may be introduced to the pericardial space by passing them over the guide wire (i.e., the lumen of the procedure-specific catheter is threaded over the guide wire). Once a specific catheter is positioned within the pericardial space, a medical procedure may be performed on the heart. Such medical procedures include, for example, the delivery of an electrical signal for pacing, cardioverting and/or ablating arrhythmias; the sensing of an electrocardiogram (ECG) signal; the acute or chronic delivery of a pharmacologic agent; the delivery of a dye or imaging agent; the withdrawal of a fluid sample for analysis; and the withdrawal of fluid for treatment of cardiac tamponade.

For delivery of electrical energy to the heart or for sensing the electrical activity from the heart, an electrode catheter can be used. Such a catheter may comprise a single electrode or an array of many electrodes. For delivery of a pharmacologic agent (i.e., a drug) to the heart, the distal end of the delivery catheter can be positioned within the pericardial space so that a drug can be directed to a specific location within the myocardium, such as the fat pad near the coronary vessels.

In an alternate embodiment of the invention, once the guide wire is in position, it may not be necessary to guide any other device into the pericardial space. The guide wire itself may be used to remove or introduce small quantities of fluid from or into the pericardial space, or to act as an electrode for sensing or delivering an electrical signal. The guide wire may also embody a fiber optic device or other instrument.

In a preferred implementation of this method of the invention, guide catheter 401 is left in position until any medical procedure is completed. Guide catheter 401 protects the tissue of the veins along the venous route to the heart from damage when one or more catheters are introduced, manipulated and eventually removed from the pericardial space. However, with guide wire 403 in position, guide catheter 401 is not required and may be removed if desired.

This embodiment of the present invention may be used to place a catheter in the heart for both acute and chronic use. For chronic implantations, guide wire 403 may be removed after a desired catheter has been positioned as desired. For example, a drug delivery catheter or a pacing electrode may be left in place for chronic use. Various known methods may be used to secure the drug delivery catheter or electrode at the puncture site in the atrial wall.

In the preferred embodiment of the invention, the apex of the right auricle is pierced to access the pericardial space. The inventors note, however, that the method of the invention may also be used to enter the pericardial space through any other portion of the right atrium.

The inventors have conducted animal experiments to confirm the efficacy of the above-described method. Using six, adult dogs, seventeen attempts were made to position a guide wire into the pericardial space using a femoral vein or a jugular vein for access. All seventeen attempts were successful with no internal bleeding and no complications. In one animal, 65 ml of anticoagulated blood was first introduced into the pericardial space to simulate tamponade. The blood was successfully removed without complication.

Placement of guide catheter 401 into position over the venous route to the right atrium took approximately five minutes. Once guide catheter 401 was in position, placement of guide wire 403 into the pericardial space took approximately three additional minutes. Fluoroscopic imaging was used during catheterization to monitor progress. The results were confirmed by thoracotomy.

Figure 5:
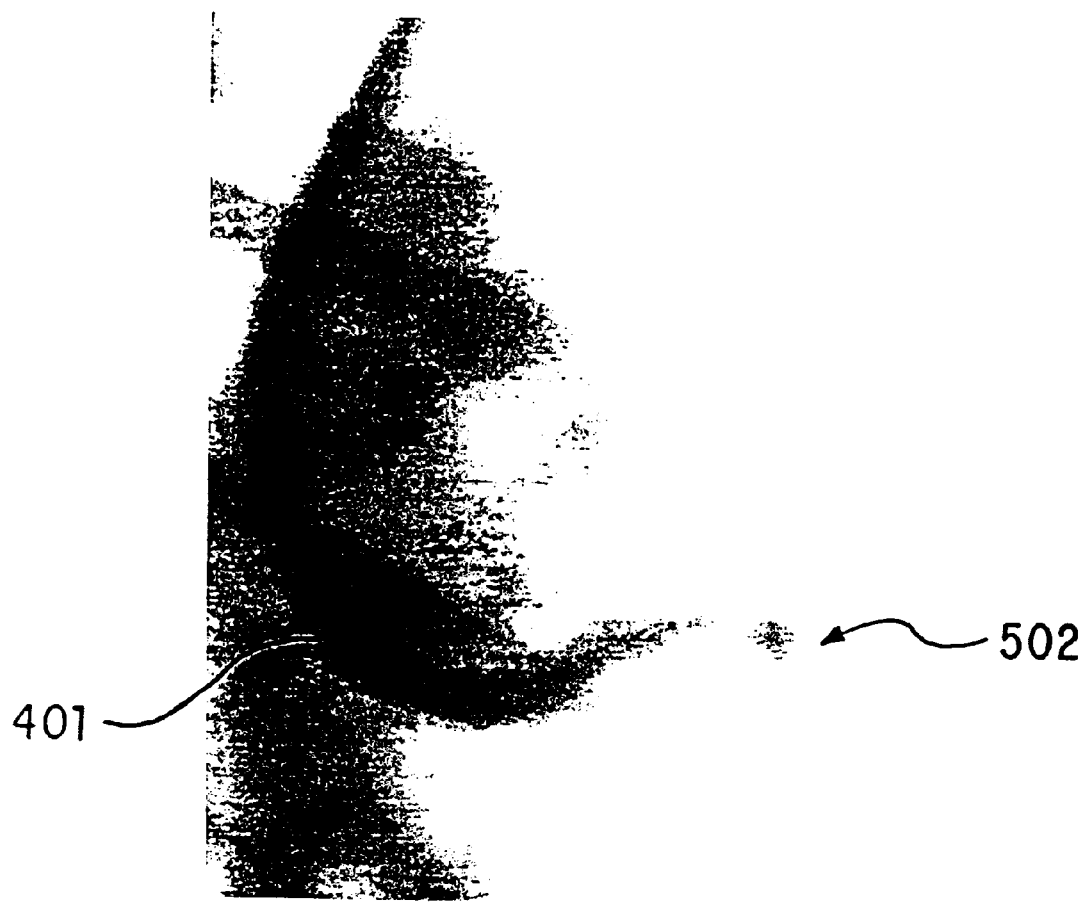
FIG. 5 is a fluoroscopic image showing positioning of a guide catheter into the right auricle.
Figure 6:
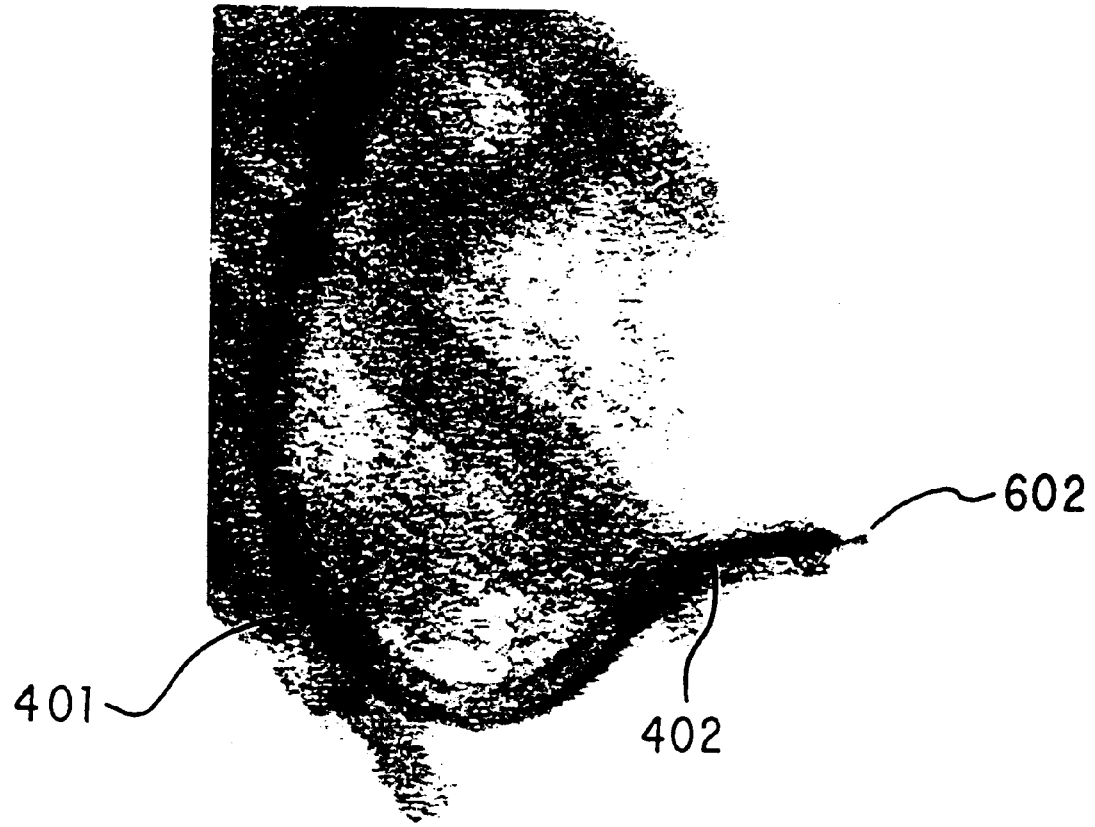
FIG. 6 is a fluoroscopic image showing positioning of a needle catheter through the guide catheter so that a distal tip of the needle catheter is penetrating a wall of the right auricle.

FIGS. 5–8 are fluoroscopic images taken during one of the animal experiments. Referring first to FIG. 5, guide catheter 401 is shown positioned within the right atrium of the heart with a distal tip 502 of catheter 401 positioned closely adjacent to the wall of the right auricle. FIG. 6 is similar to FIG. 5 but, in FIG. 6, needle catheter 402 has been advanced through guide catheter 401 so that a distal tip 602 is extending out from distal tip 502 of guide catheter 401. In this image, distal tip 602 of needle catheter 402 has penetrated the wall of the right auricle.

Figure 7:
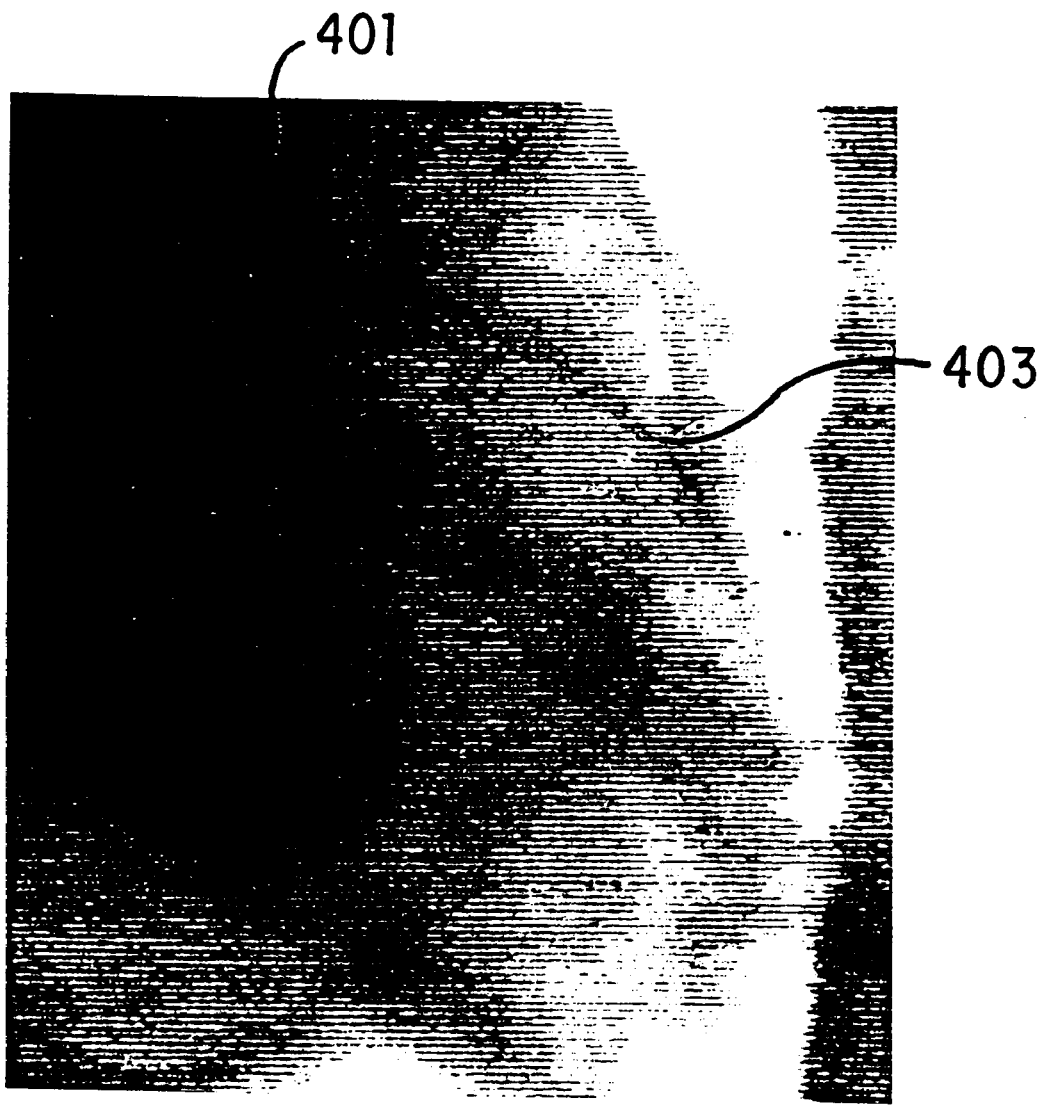
FIG. 7 is a fluoroscopic image showing introduction of a guide wire into the pericardial space through the right auricle.
Figure 8:
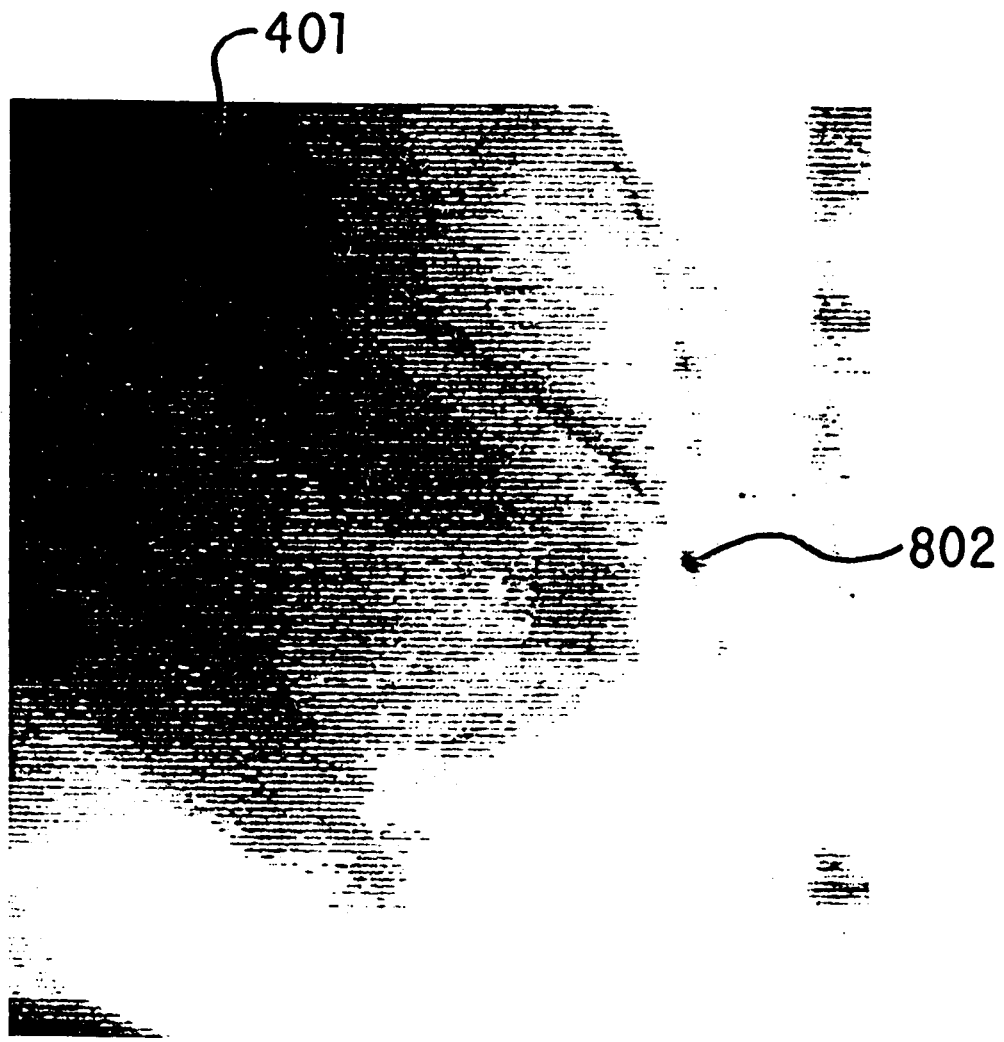
FIG. 8 is a fluoroscopic image showing introduction of an angioplasty catheter over the guide wire and into the pericardial space.

FIG. 7 shows extension of guide wire 403 out from guide catheter 401 and into the pericardial space. Note how guide wire 403 conforms to the shape of the contour of the heart. FIG. 8 is similar to FIG. 7, but in FIG. 8, an angioplasty catheter 801 having a radiopaque marker 802 at its distal tip has been advanced over guide wire 403 and into the pericardial space.

As mentioned above, there are many advantages of using a guide wire to assist in performing medical procedures via the pericardial space. First, the successful placement of a guide wire into the pericardial space can be confirmed without the need to inject a radiopaque dye. Also, a guide wire maintains a stable point of entry into the pericardial space to permit repeated, successive introduction of different intrapericardial catheters. Additionally, use of a guide wire helps to prevent trauma to the epicardium and pericardium of a patient's heart. That is, use of a guide wire permits catheters to easily be swapped in and out with little risk to a patient. Furthermore, a guide wire permits accurate positioning of an intrapericardial catheter at any location within the pericardial space.

The inventors have also discovered that a guide wire can be used to perform the actual piercing of the wall of right auricle 108. That is, the following methods use an appropriate guide wire, rather than needle catheter 402, to pierce the wall of right auricle 108. Because a guide wire is already located within the pericardial space once the guide wire pierces the wall of right auricle 108, there is no need to advance an additional guide wire 403 into the pericardial sac. Thus, the following methods can reduce the total number of steps required to perform a medical procedure on the heart via the pericardial space. Accordingly, the following methods can reduce the total amount of time that it takes to perform a medical procedure on the heart via the pericardial space. Additionally, the following methods can be performed using a novel combination of appropriate off-the-shelf guide wires and thereby avoid the necessity for a customized needle catheter 402.

The high level flow chart of FIG. 2 can also be used to describe the steps of gaining access to the pericardial space using alternative methods. However, as will be explained below, the implementation of step 202 is different. Additionally, the implementation of steps 204 and 206 may be different than the implementation used in the method described above in the discussion of FIGS. 3–8.

Figure 9:
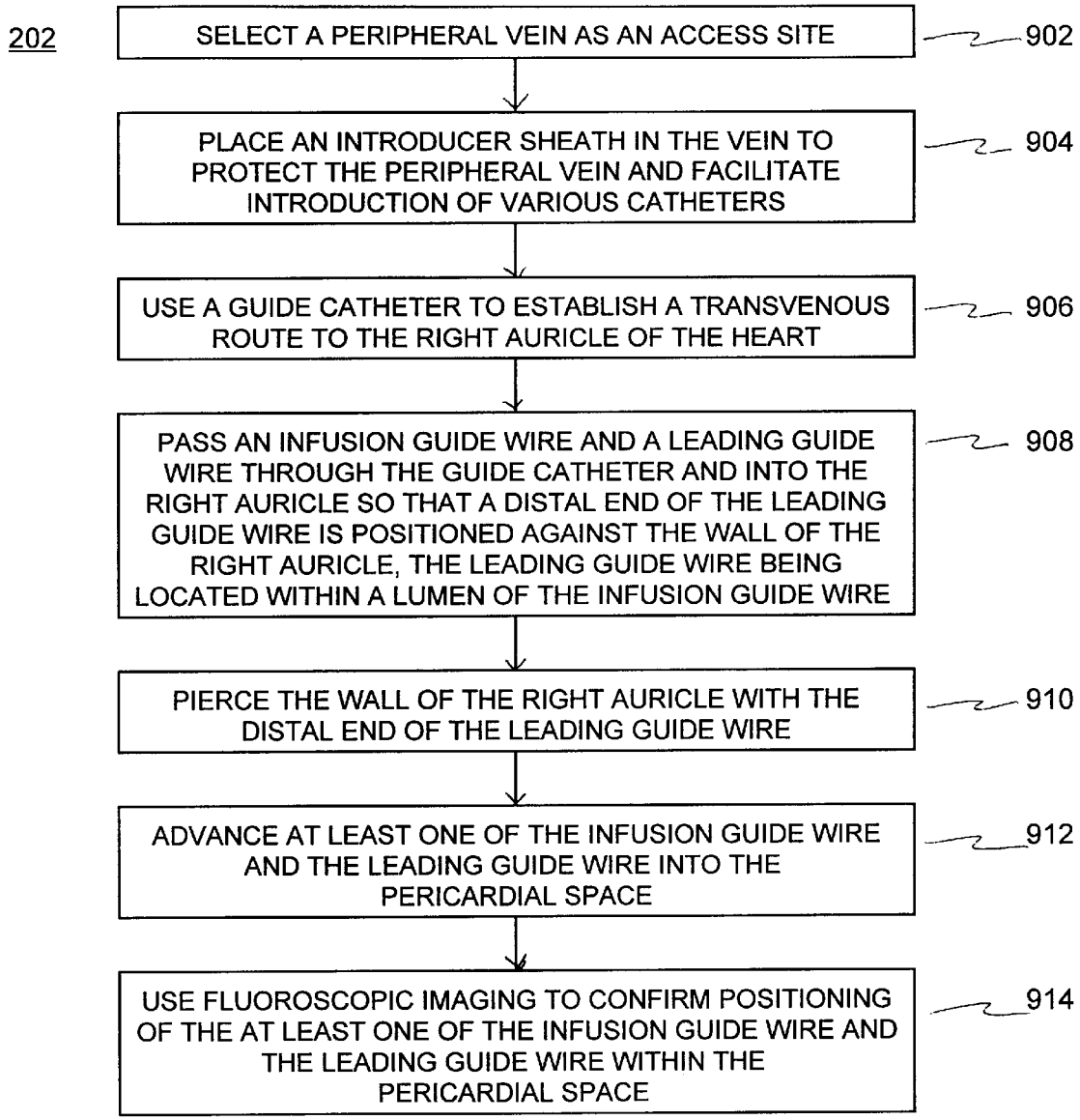
FIG. 9 is a flow chart showing a method of the invention for introducing one or more guide wires into the pericardial space via a transvenous route, according to an alternative embodiment of the present invention.
Figure 10:
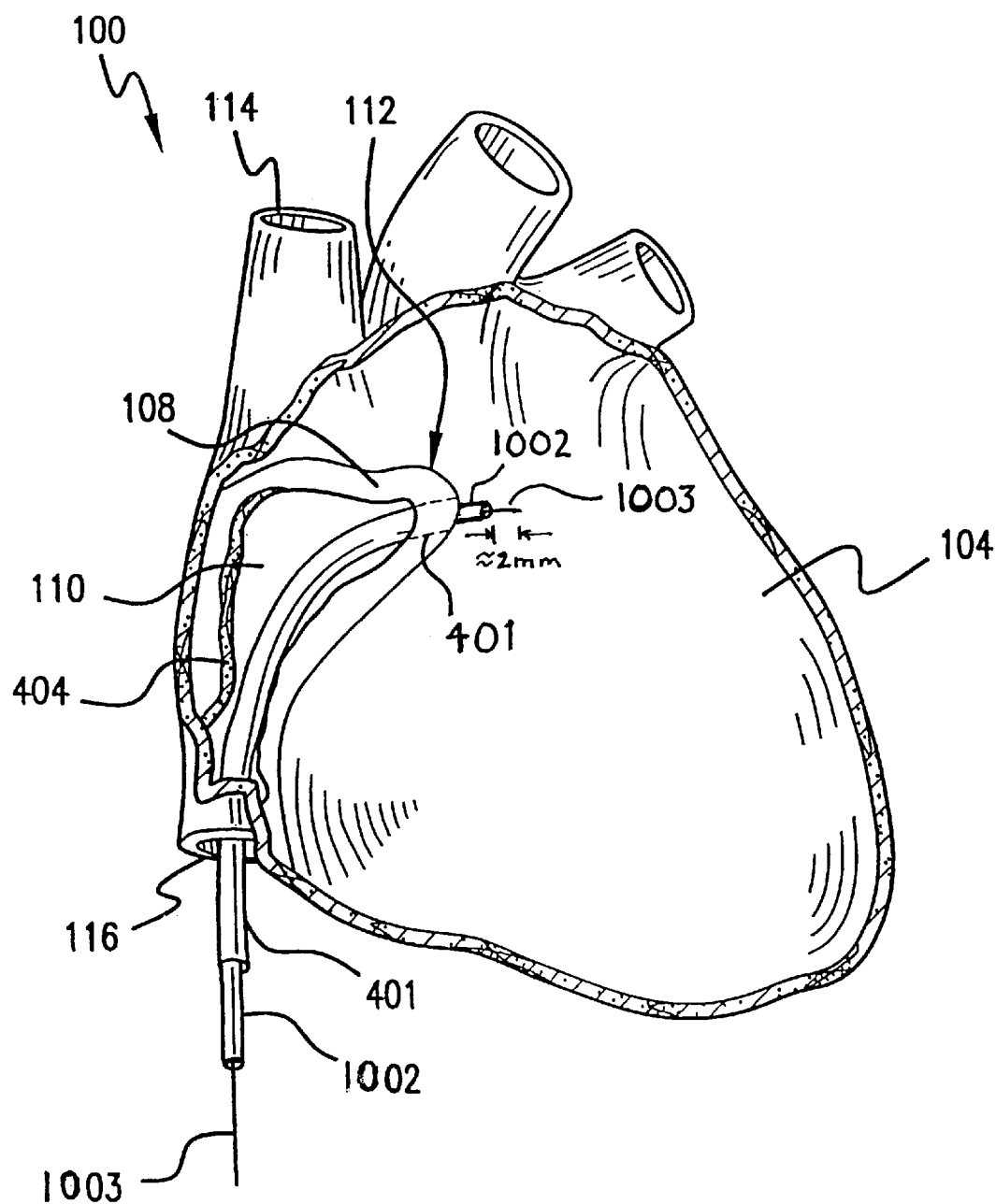
FIG. 10, which is used to explain the method of FIG. 9, is a simplified diagram of a human heart as shown in FIG. 1 but with a portion of the right atrium cut away to show the introduction of a catheter and into the right auricle and the introduction of an infusion guide wire and a leading guide wire through the wall of the right auricle and into the pericardial space.

For these alternative methods, step 202 of positioning a guide wire in the pericardial space is shown in greater detail with reference to additional FIGS. 9 and 10. FIG. 9 illustrates the steps of the alternative methods. FIG. 10 shows the heart 100 of FIG. 1 with a cutaway 404 to illustrate passage of guide catheter 401 and guide wires 1002, 1003 through inferior vena cava 116, through right atrium 110 and into right auricle 108 as described with reference to FIG. 9. FIG. 10 also shows the distal ends of guide wires 1002, 1003 advanced through the wall of right auricle 108 and into the pericardial space.

In one embodiment, two guide wires are used to access the pericardial space. One guide wire, having a larger diameter and a hollow lumen, is referred to as infusion guide wire 1002. The other guide wire, which has a smaller diameter and is used to pierce the wall of right auricle 108, is referred to as leading guide wire 1003. Leading guide wire 1003 may or may not have a hollow lumen. As will be described below, in the preferred embodiment the two guide wires 1002, 1003 are used together as a system.

Steps 902, 904, and 906 are substantially the same as steps 302, 304, and 306, respectively, which are discussed in detail above. Accordingly, reference should be made to steps 302, 304, and 306 for additional details. In a step 902, a peripheral vein is selected as an access site. In a step 904, the access site is prepared by placing an introducer sheath into the vein. In a step 906, a guide catheter 401 is passed through the introducer sheath, through the peripheral vein, through any downstream veins and into one of the venae cavae.

Guide catheter 410 must have a sufficient length and a sufficient flexibility to be inserted into the right atrium of a subject's heart via a transvenous route. In this embodiment, an 8French, multipurpose catheter, available from Boston Scientific Corporation, Natick, Mass., has typically been employed for guide catheter 401. However, larger or smaller catheters of different shapes, depending on the vein of entry, can be selected to accommodate the devices to be introduced therethrough. In an alternate embodiment of the invention, guide catheter 401 may include means for monitoring blood pressure and electrocardiogram. These features permit placement of the guide catheter into position in the right atrium using electrical and/or hemodynamic indices.

In a step 908, an infusion guide wire 1002 and a leading guide wire 1003 are simultaneously passed through guide catheter 401. Leading guide wire 1003 is located within a lumen of infusion guide wire 1002 and can be extended from a distal end of infusion guide wire 1002. Leading guide wire 1003 is preferably pre-disposed within the lumen of infusion guide wire 1002 and preferrably protrudes approximately 2 mm from the distal end of infusion guide wire 1002. Preferably, the pair of guide wires 1002, 1003 are simultaneously advanced through guide catheter 401 until a distal tip of leading guide wire 1002 is urged against the wall of right auricle 108 by placing a slight axial force on the proximal ends of the pair of guide wires 1002, 1003. Alternatively, infusion guide wire 1002 and leading guide wire 1003 are separately advanced through guide catheter 401. It is noted that the piercing of the wall of right auricle is performed without attaching a distal end of a guide catheter 401 to said wall of the right auricle.

Infusion guide wire 1002 and leading guide wire 1003 should have sufficient flexibility to permit them to be passed through guide catheter 401 and into right atrium 110 of the subject's heart via a transvenous route. Infusion guide wire 1002 should have a diameter sufficiently small to be passed through a lumen of guide catheter 401. Further, infusion guide wire 1002 should have a sufficient length to be passed through guide catheter 401 and into right atrium 110 of the subject's heart via a transvenous route. Leading guide wire 1003 should have a diameter sufficiently small to be passed through a lumen of infusion guide wire 1003. Further, leading guide wire 1003 should have a sufficient length to pass through and protrude from a distal end of infusion guide wire 1002. Preferably, leading guide wire 1003 has a length that is substantially longer than infusion guide wire 1002. This is so that a portion of leading guide wire 1003, which protrudes from a proximal end of infusion guide wire 1003, can be used to maneuver leading guide wire 1003 either independently from or simultaneously with infusion guide wire 1002. This also enables leading guide wire 1003 to be easily used as an exchange wire.

In one embodiment, the proximal end of infusion guide wire 1002 includes a locking device (not shown) to lock leading guide wire 1003 within infusion guide wire 1003. Such a locking device may include a lock lever that when engaged holds leading guide wire 1003 at a specific position within infusion guide wire 1002. This locking device is useful when attempting to simultaneously maneuver infusion guide wire 1002 and leading guide wire 1003. Further, a proximal end of the locking device can include a screwable knob that enables a syringe to be easily attached to infusion guide wire 1002. The syringe can be used to aspirate a substance from or deliver a substance to the pericardial sac. Alternatively, the locking function described above can be accomplished using the thumb and an additional finger (e.g., index finger) of the individual performing the procedure.

In a step 910, the distal end (more specifically, the tip of the distal end) of leading guide wire 1003 is used to pierce the wall of right auricle 108 to gain access to the pericardial space. In one embodiment, this is accomplished by simultaneously applying an axial force to a proximal end of infusion guide wire 1002 and to a portion of leading guide wire 1003 that protrudes from the proximal end of infusion guide wire 1003 until the distal end of the leading guide wire pierces the wall of right auricle 108. In other words, both infusion guide wire 1002 and leading guide wire 1003 are grasped near the proximal end of infusion guide wire and advanced into guide catheter 401 until leading guide wire 1003 pierces the wall of right auricle 108. Alternatively, an axial force can be applied to only the portion of leading guide wire 1003 that protrudes from the proximal end of infusion guide wire 1003, thereby causing leading guide wire 1003 to advance independent from infusion guide wire 1002. Where the locking device described above is used, an axial force can be applied to the locking device.

In another embodiment, the piercing of the wall of right auricle 108 is accomplished by holding the distal tip of leading guide wire 1003 in contact with the atrial wall at apex 112. As the heart contracts, the atrial wall will be further urged against the distal tip of leading guide wire 1003. After a short period of time has elapsed (e.g., 30 to 60 seconds), leading guide wire 1003 will pierce through the wall of right auricle 108 as a result of the mechanical motion of the heart while it beats. However, in this embodiment of the present invention, use of the mechanical motion of the heart is less important than when a needle catheter is used to pierce since the flexible leading guide wire 1003 is less likely to go through the wall of right auricle 108 and damage other heart tissue or a coronary vessel within the pericardial space. More generally, the inventors believe that the risk of damage to the heart is greatly reduced when a flexible leading guide wire, as opposed to a non-flexible needle, is used to penetrate the wall of right auricle 108. This is true whether the penetration is caused by the mechanical motion of the heart, or by an axial force applied to a proximal portion of leading guide wire 1003.

Even though not optimal, it is noted that once leading guide wire 1003 and infusion guide wire 1002 are advanced through guide catheter 401 and in into right auricle 108, a distal end (more specifically, the tip of the distal end) of infusion guide wire 1002, rather than the distal end of leading guide wire 1003, can be used to pierce the wall of right auricle 108. Also, if the distal ends of leading guide wire 1003 and infusion guide wire 1002 are aligned, then the distal ends of leading guide wire 1003 and infusion guide wire 1002 can be used to simultaneously pierce the wall of right auricle 108.

Leading guide wire 1003 should have a sufficient stiffness such that its distal tip is capable of penetrating the wall of right auricle 108 of the subject's heart, while having a sufficient flexibility to not damage the epicardium and pericardium within the pericardial sac. Leading guide wire 1003 preferably has a diameter in the range of 0.010 inches to 0.018 inches, with an optimal diameter of approximately 0.014 inches. Infusion guide wire 1002 preferably has a diameter of approximately 0.04 inches.

In the animal experiments discussed below, the inventors used a leading guide wire 1003 having a 0.014 inch diameter and a length of 300 centimeters, available from Cordis Corporation, Miami Lakes, Fla., (sold as the "Stabilizer" guide wire) and an infusion guide wire 1002 having a 0.038 inch diameter and a 145 centimeter length, available from C. R. Bard Incorporated, headquartered in Murray Hill, N.J. (sold as the "SOS Open Ended Guidewire"). Prior to advancing the pair of guide wires 1002, 1003 through guide catheter 401, leading guide wire 1003 is positioned within infusion guide wire 1002 by advancing leading guide wire 1003 through infusion guide wire 1002 until approximately 2 mm of the distal end of leading guide wire 1003 extends out from the distal end of infusion guide wire 1002. This effectively increases the stiffness of leading guide wire 1003 while not effecting the sharpness of its distal tip. A locking device as described above is preferably used to keep leading guide wire 1003 in place within infusion guide wire 1002.

Returning to the flowchart of FIG. 9, in a step 912, at least one of infusion guide wire 1002 and/or leading guide wire 1003 is advanced through the atrial wall and into pericardial space 106. In step 914, as infusion guide wire 1002 and/or leading guide wire 1003 are being pushed into the pericardial space, fluoroscopic or echocardiographic imaging can be used to confirm that infusion guide wire 1002 and/or leading guide wire are actually being advanced into the pericardial space as they exit the distal end of guide catheter 401. In a preferred embodiment, infusion guide wire 1002 and leading guide wire 1003 are simultaneously advanced into the pericardial space. Infusion guide wire 1002 and leading guide wire 1003 should each have sufficient flexibility to permit them to conform at least partially to the contour of the heart when they extend outward from a distal tip of guide catheter 401 and into the pericardial space. Accordingly, as infusion guide wire 1002 and/or leading guide wire 1003 are pushed two to three inches into the pericardial space, they will begin to take the shape of the space. When infusion guide wire 1002 and/or leading guide wire 1003 begin to take the shape of the contour of the heart, the clinician will note this in the fluoroscopic or echocardiographic image. In this manner, the clinician confirms proper placement of infusion guide wire 1002 and/or leading guide wire 1003 within the pericardial space.

Once at least one of infusion guide wire 1002 and/or leading guide wire 1003 are in position within the pericardial space, any number of different procedure-specific catheters (including surgical instruments such as fiber optic imaging devices) may be introduced to the pericardial space by passing them over the infusion guide wire 1002 and/or leading guide wire 1003 (i.e., the lumen of the procedure-specific catheter is threaded over one or both guide wires 1002, 1003).

Once a specific catheter is positioned within the pericardial space, a medical procedure may be performed on the heart. Such medical procedures include, for example, the delivery of an electrical signal for pacing, cardioverting and/or ablating arrhythmias; the sensing of an electrocardiogram (ECG) signal; the acute or chronic delivery of a pharmacologic agent; the delivery of a dye or imaging agent; the withdrawal of a fluid sample for analysis and/or diagnostic applications; the withdrawal of fluid for treatment of cardiac tamponade; the imaging/inspecting of heart muscles and coronary arteries for detection of damage and disease; the mapping of electrophysical properties of the heart including excitation and repolarization; and the performing of a surgical procedure.

For delivery of electrical energy to the heart or for sensing the electrical activity from the heart, an electrode catheter can be used. Such a catheter may comprise a single electrode or an array of many electrodes. For imaging/inspecting of heart muscles and coronary arteries, a catheter including a fiber optic device or ultrasound device can be used. For mapping of electrophysical properties a catheter including an electromagnetic field apparatus can be used. For performing of a surgical procedure, a laser catheter or other type of surgical catheter can be used. For delivery of a pharmacologic agent (i.e., a drug) to the heart, the distal end of the delivery catheter can be positioned within the pericardial space so that a drug can be directed to a specific location within the myocardium, such as the fat pad near the coronary vessels. Such a pharmacologic agent can be an anti-inflammatory agent, an antibacterial agent, an antiviral agent, or a growth agent. Other types of substances that can be delivered to the pericardial space include, for example, biological agents, lubricants, polymers, and synthetic agents.

In the preferred embodiment, where infusion guide wire 1002 and leading guide wire 1003 are simultaneously advanced into the pericardial space, one or both of guide wires 1002, 1003 may act as an electrode for sensing or delivering an electrical signal. Further, leading guide wire 1003 can be removed so that the lumen of infusion guide wire 1002 can be used to deliver a substance or remove a substance from the pericardial space. Accordingly, it may not be necessary to guide any other device into the pericardial space.

Where it is necessary to guide a specific catheter into the pericardial space, the specific catheter may be guided over one or both of infusion guide wire 1002 and leading guide wire 1003. Accordingly, either of infusion guide wire 1002 or leading guide wire 1003 may be removed prior to a specific catheter being guided into the pericardial space. Where a lumen of a specific catheter is to be used to remove a substance or deliver a substance to the pericardial space while a guide wire remains in place, the specific catheter is preferably guided over only the leading guide wire 1003. Once a specific catheter is guided into proper position within the pericardial space, infusion guide wire 1002 and/or leading guide wire 1003 can be removed if desired.

In a preferred implementation, guide catheter 401 is left in position until any medical procedure is completed. Guide catheter 401 protects the tissue of the veins along the venous route to the heart from damage when one or more catheters are introduced, manipulated and eventually removed from the pericardial space. Guide catheter 401 also provides support to traverse the atrial wall with guide wires 1002, 1003 and the various catheters discussed above. However, when at least one of infusion guide wire 1002 and leading guide wire 1003 is in position, guide catheter 401 is not required and may be removed if desired.

These alternative embodiments of the present invention may be used to place a catheter in the heart for both acute and chronic use. For chronic implantations, infusion guide wire 1002 and leading guide wire 1003 may be removed after a desired catheter has been positioned as desired. For example, a drug delivery catheter or a pacing electrode may be left in place for chronic use. Various known methods may be used to secure the drug delivery catheter or electrode at the puncture site in the atrial wall.

If leading guide wire 1003 is not sufficiently flexible, it may perforate the epicardium and/or pericardium once within the pericardial space. If leading guide wire 1003 is too flexible, it may not be capable of piercing the wall of right auricle 108. Additionally, if the leading guide wire is too flexible, it may collapse or fold once within the pericardial space rather than conforming to the contour of the heart. A collapsed or folded guide wire would not be useful for confirming proper placement within the pericardial space or for guiding catheters into the pericardial space. Accordingly, tests were performed to determine the optimal characteristics of leading guide wire 1003.

The results of the tests showed that a preferred suitable diameter of leading guide wire 1003 is 0.0136 inches. More specifically, a leading guide wire 1003 having a 0.0136 inch diameter provided the appropriate perforating force with a minimal amount of axial force. Additionally, a leading guide wire 1003 having a 0.0136 inch diameter provided sufficient flexibility to not inadvertently perforate the epicardium and/or pericardium of a patient's heart. Further, a leading guide wire 1003 having a 0.0136 inch diameter provided the appropriate flexibility to conform to the contour of the heart. Although they may not all be optimal, leading guide wires 1003 having a diameter between 0.010 inches and 0.018 inches have acceptable characteristics to be effectively used in the present invention.

The inventors have conducted animal experiments to confirm the efficacy of the above-described methods. Using twenty anesthetized pigs, attempts were made to position both an infusion guide wire and a leading guide wire into the pericardial space using a femoral vein or a jugular vein for access. Pericardial access was documented by fluoroscopic imaging and pericardial fluid sampling. The results of the fluoroscopic imaging were similar to the results described above in the discussion of FIGS. 5–8 in that advancement of infusion guide wire 1002 and leading guide wire 1003 were accurately monitored by a clinician.

Pericardial access was successfully accomplished in all animals with no internal bleeding and no complications. Placement of guide catheter 401 into position over the venous route to the right atrium took approximately five minutes. Once guide catheter 401 was in position, placement of infusion guide wire 1002 and leading guide wire 1003 into the pericardial space was successfully accomplished in all animals within three additional minutes. After the procedure was performed on the animals they were allowed to recover from anesthesia. For histopathologic analysis, ten animals were sacrificed twenty four hours following the procedure and ten animals were sacrificed two weeks following the procedure. Mean pericardial hematocrit was 1% at initial sampling, 4.5% at twenty four hours, and 0.5% at two weeks. There were no hemodynamic or electrocardiographic changes during or after the procedure. At twenty-four hours, there was local inflammatory reaction in the atrial wall and a small thrombus at the site of puncture. At two weeks, no significant inflammatory changes or pericarditis were evident. Accordingly, the preclinical safety of the above described method to access a normal pericardial space for the purpose of diagnostic sampling and local cardiac drug delivery was demonstrated. This procedure was tolerated both immediately and up to two weeks following the procedure, and was intrinsically devoid of adverse complications. Further advances in the field of intrapericardial therapeutics and diagnostics will direct the clinical application of this novel method in human subjects.

The inventors have discovered that a preferred system is realized by disposing leading guide wire 1003 within the lumen of infusion guide wire 1002 and protruding the distal end of leading guide wire 1003 approximately 2 mm out of the distal end of infusion guide wire 1002, as discussed above. Accordingly, in the preferred method both infusion guide wire 1002 and leading guide wire 1003 are used to transvenously access the pericardial space to perform a medical procedure on the heart. One of the important reasons for using the two guide wire system is to produce a device that has the suitable stiffness and sharpness to penetrate the wall of right auricle 108, and sufficient flexibility to not damage the epicardium and/or pericardium of a patient's heart. By effectively increasing the stiffness of the leading guide wire 1003, infusion guide wire 1002 assists leading guide wire in its piercing function. Additionally, the two guide wire system is inexpensive to produce. Further, use of the two guide wire system is efficient because it reduces the total number of steps and accordingly the total amount to time required to perform a medical procedure. For example, once the wall of right auricle 108 is pierced, infusion guide wire 1003 can be quickly advanced into the pericardial space to be used for performing many of the medical procedures discussed above (e.g., the removal of a substance from or delivery of a substance to the pericardial space). Therefore, in the preferred embodiment infusion guide wire 1003 is always used.

The two guide wire embodiments discussed above also provide a safe method of accessing the pericardial space. This is because the tangential introduction of relatively small (in diameter) and flexible guide wires 1002, 1003 across the right atrial appendage and into the pericardial space minimizes the risk of coronary laceration and myocardial perforation. Additionally, the small diameter and flexibility of leading guide wire 1003 also adds a margin of safety when the wall of right auricle 108 is pierced.

In yet another embodiment, a single guide wire having the correct characteristics can be used to pierce the wall of right auricle 108. Preferably such a single guide wire would include a lumen that can be used for delivery of a substance to or removal of a substance from the pericardial space. When using such a single guide wire approach, the piercing of the wall of right atrium 108 can be accomplished by applying an axial force to the distal portion of the single guide wire, or by urging the distal tip of the single guide wire against the atrial wall and allowing the mechanical beating motion of the heart to cause the piercing.

The inventors note that all of the above discussed advantages may not be realized with such a single guide wire approach. For example, a guide wire that is sufficiently small for penetration may not have a sufficiently large lumen for effectively delivering a substance to or removing a substance from the pericardial space. Thus, if a single guide wire were advanced through guide catheter 401 and into the pericardial space, an additional step of advancing an aspiration or delivery catheter over leading guide wire 1003 may be necessary. This would add an additional step and thus take additional time. Further, a single guide wire that is not disposed within another guide wire would not have the optimal stiffness and thus may not pierce the wall of right atrium 108 as easily.

Conclusion

Although the invention has been described and illustrated with a certain degree of particularity, it is understood that those skilled in the art will recognize a variety of applications and appropriate modifications within the spirit of the invention and the scope of the claims.

What is claimed is:

1. A method for transvenously accessing the pericardial space between a heart and its pericardium to perform a medical procedure on the heart, the method comprising the following steps:
   (a) passing a guide catheter through a selected vein to establish a transvenous route to the right auricle of the heart;
   (b) passing an infusion guide wire and a leading guide wire through said guide catheter and into the right auricle so that at least one of a distal end of said leading guide wire and a distal end of said infusion guide wire is positioned against a wall of the right auricle, said leading guide wire being located within a lumen of said infusion guide wire;
   (c) piercing said wall of the right auricle with at least one of said distal end of said leading guide wire and said distal end of said infusion guide wire;
   (d) advancing at least one of said infusion guide wire and said leading guide wire into the pericardial space; and
   (e) using said at least one of said infusion guide wire and said leading guide wire to perform a specific medical procedure on the heart.

2. The method of claim 1, wherein said step (c) of piercing said wall of the right auricle is performed without attaching a distal end of said guide catheter to said wall of the right auricle.

3. The method of claim 2, wherein said leading guide wire has a greater length than said infusion guide wire, and wherein said step (c) of piercing comprises the step of:
   simultaneously applying an axial force to said infusion guide wire and said leading guide wire until at least one of said distal end of said leading guide wire and said distal end of said infusion guide wire pierces said wall of the right auricle.

4. The method of claim 1, wherein step (d) of advancing at least one of said infusion guide wire and said leading guide wire comprises the step of:
   simultaneously advancing said infusion guide wire and said leading guide wire into the pericardial space.

5. The method of claim 4, further comprising the step between steps (d) and (e) of removing said leading guide wire.

6. The method of claim 1, wherein step (d) comprises advancing said infusion guide wire into the pericardial space, and wherein the method further comprises the step between steps (d) and (e) of removing said leading guide wire.

7. The method of claim 6, wherein said step (e) of using said at least one of said infusion guide wire and said leading guide wire comprises the step of:
   (e) using said infusion guide wire to deliver a substance to the pericardial space via said lumen of said infusion guide wire, wherein said substance is selected from a group consisting of a medication, a biological agent, a lubricant, a polymer, and a synthetic agent.

8. The method of claim 6, wherein said step (e) of using said at least one of said infusion guide wire and said leading guide wire comprises the step of:
   (e) using said infusion guide wire to perform said specific medical procedure on the heart, said specific medical procedure being selected from the group consisting of (1) withdrawing a fluid from the pericardial space via said lumen of said infusion guide wire, (2) delivering a substance to the pericardial space via said lumen of said infusion guide wire, (3) using a conductor of said infusion guide wire to deliver an electrical signal to the heart from within said pericardial space, and (4) using a conductor of said infusion guide wire to sense an electrical signal from the heart from within said pericardial space.

9. The method of claim 8, further comprising the steps of:

(f) advancing said leading guide wire back through said infusion guide wire into the pericardial space;

(g) removing said infusion guide wire; and (h) using said leading guide wire as a conduit over which a desired catheter may be introduced for performing a further specific medical procedure.

10. The method of claim 9, wherein said step (h) comprises the steps of:

using said leading guide wire as a conduit over which a desired catheter may be introduced for performing said further specific medical procedure, said desired catheter and said further specific medical procedure being selected from the group consisting of (1) passing an electrode catheter over said leading guide wire and into the pericardial space so that a distal end of said electrode catheter is maintained in contact with the epicardium, and using said electrode catheter to deliver electrical energy to said epicardium;

(2) passing an electrode catheter over said leading guide wire and into the pericardial space so that a distal end of said electrode catheter is maintained in contact with the epicardium, and using said electrode catheter to sense electrical energy from said epicardium;

(3) passing a drug delivery catheter over said leading guide wire so that a distal end of said drug delivery catheter is positioned in the pericardial space, and using said drug delivery catheter to deliver a pharmacologic agent to the pericardial space;

(4) passing a fluid removal catheter over said leading guide wire so that a distal end of said fluid removal catheter is positioned in the pericardial space, and using said fluid removal catheter to remove fluid from the pericardial space; and (5) passing an imaging catheter over said infusion guide wire so that said imaging catheter is positioned in the pericardial space, and using said imaging catheter to observe at least one of heart muscles, coronary arteries, and the pericardium.

11. The method of claim 1, wherein step (e) comprises the step of using said infusion guide wire as a conduit over which a desired catheter may be introduced for performing said specific medical procedure.

12. The method of claim 11, wherein said step (e) further comprises the steps of:

(e) using said infusion guide wire as a conduit over which a desired catheter may be introduced for performing said specific medical procedure, said desired catheter and said specific medical procedure being selected from the group consisting of (1) passing an electrode catheter over said infusion guide wire and into the pericardial space so that a distal end of said electrode catheter is maintained in contact with the epicardium, and using said electrode catheter to deliver electrical energy to said epicardium;

(2) passing an electrode catheter over said infusion guide wire and into the pericardial space so that a distal end of said electrode catheter is maintained in contact with the epicardium, and using said electrode catheter to sense electrical energy from said epicardium;

(3) passing a drug delivery catheter over said infusion guide wire so that a distal end of said drug delivery catheter is positioned in the pericardial space, and using said drug delivery catheter to deliver a pharmacologic agent to the pericardial space;

(4) passing a fluid removal catheter over said infusion guide wire so that a distal end of said fluid removal catheter is positioned in the pericardial space, and using said fluid removal catheter to remove fluid from the pericardial space; and (5) passing an imaging catheter over said infusion guide wire so that said imaging catheter is positioned in the pericardial space, and using said imaging catheter to observe at least one of heart muscles, coronary arteries, and the pericardium.

13. The method of claim 1, further comprising the step between steps (d) and (e) of removing said infusion guide wire.

14. The method of claim 13, wherein said step (e) of using said at least one of said infusion guide wire and said leading guide wire comprises the step of:

(e) using said leading guide wire to perform said specific medical procedure on the heart, said specific medical procedure being selected from the group consisting of (1) using a conductor of said leading guide wire to deliver an electrical signal to the heart from within said pericardial space, and (2) using a conductor of said leading guide wire to sense an electrical signal from the heart from within said pericardial space.

15. The method of claim 13, wherein step (e) comprises the step of using said leading guide wire as a conduit over which a desired catheter may be introduced for performing said specific medical procedure.

16. The method of claim 15, wherein said step (e) further comprises the steps of:

(e) using said leading guide wire as a conduit over which a desired catheter may be introduced for performing said specific medical procedure, said desired catheter and said specific medical procedure being selected from the group consisting of (1) passing an electrode catheter over said leading guide wire and into the pericardial space so that a distal end of said electrode catheter is maintained in contact with the epicardium, and using said electrode catheter to deliver electrical energy to said epicardium;

(2) passing an electrode catheter over said leading guide wire and into the pericardial space so that a distal end of said electrode catheter is maintained in contact with the epicardium, and using said electrode catheter to sense electrical energy from said epicardium;

(3) passing a drug delivery catheter over said leading guide wire so that a distal end of said drug delivery catheter is positioned in the pericardial space, and using said drug delivery catheter to deliver a pharmacologic agent to the pericardial space;

(4) passing a fluid removal catheter over said leading guide wire so that a distal end of said fluid removal catheter is positioned in the pericardial space, and using said fluid removal catheter to remove fluid from the pericardial space; and (5) passing an imaging catheter over said infusion guide wire so that said imaging catheter is positioned in the pericardial space, and using said imaging catheter to observe at least one of heart muscles, coronary arteries, and the pericardium.

17. The method of claim 1, wherein said step (a) of passing a guide catheter comprises the steps of:

placing an introducer sheath into the selected vein;

introducing a guide catheter into said vein through said sheath;

guiding said guide catheter downstream through said vein to one of the venae cavae;

guiding said guide catheter downstream through said one of the venae cavae to the right atrium; and guiding said guide catheter through the right atrium and into the right auricle.

18. The method of claim 17, wherein said step (a) of passing a guide catheter further comprises the step of:

advancing said guide catheter into the right auricle so that a distal end of said guide catheter is placed against the wall of the right auricle; and using one of fluoroscopic imaging and echocardiographic imaging to visually follow the progress of said guide catheter into the right auricle; and confirming proper placement of said guide catheter against the wall of the right auricle when said distal end of said guide catheter moves with the beating of the heart.

19. The method of claim 18, wherein said step (c) of piercing comprises the step of:

waiting, once said distal end of said leading guide wire is positioned against said wall of the right auricle, for movement of the heart from its rhythmic beating to cause said distal end of said leading guide wire to pierce said wall of the right auricle.

20. The method of claim 1, wherein said step (d) of advancing at least one of said infusion guide wire and said leading guide wire into the pericardial space further comprises the steps of:

using one of fluoroscopic imaging and echocardiographic imaging to visually follow the progress of said at least one of said infusion guide wire and said leading guide wire into the pericardial space; and confirming proper placement of said at least one of said infusion guide wire and said leading guide wire in the pericardial space when said at least one of said infusion guide wire and said leading guide wire begins to take the shape of the contour of the heart.

21. The method of claim 20, wherein said step (d) of advancing said infusion guide wire further comprises the step of:

simultaneously advancing said leading guide wire and said infusion guide wire into the pericardial space.

22. The method of claim 21, wherein said step (d) of simultaneously advancing said leading guide wire and said infusion guide wire further comprises the steps of:

using one of fluoroscopic imaging and echocardiographic imaging to visually follow the progress of said leading guide wire and said infusion guide wire into the pericardial space; and confirming proper placement of said leading guide wire and said infusion guide wire in the pericardial space when said leading guide wire and said infusion guide wire begin to take the shape of the contour of the heart.

23. A method for transvenously removing fluid from the pericardial space between a heart and its pericardium to treat cardiac tamponade, the method comprising the following steps:

(a) passing a guide catheter through a vein to establish a transvenous route to the right auricle of the heart;

(b) simultaneously passing an infusion guide wire and an leading guide wire through said guide catheter and into the right auricle so that a distal end of said leading guide wire is positioned against a wall of the right auricle, said leading guide wire being located within a lumen of said infusion guide wire;

(c) piercing said wall of the right auricle with said distal end of said leading guide wire;

(d) advancing said infusion guide wire into the pericardial space; and (e) removing the fluid from the pericardial space.

24. The method of claim 23, wherein said step (c) of piercing said wall of the right auricle is performed without attaching a distal end of said guide catheter to said wall of the right auricle.

25. The method of claim 23, wherein step (e) of removing fluid comprises the steps of:

removing said leading guide wire; and using said infusion guide wire to remove the fluid from the pericardial space, the fluid being removed through said lumen in said infusion guide wire.

26. The method of claim 23, wherein said leading guide wire has a greater length than said infusion guide wire, and wherein said step (c) of piercing comprises the step of:

simultaneously applying an axial force said infusion guide wire and said leading guide wire until said distal end of said leading guide wire pierces said wall of the right auricle.

27. A method for transvenously accessing the pericardial space between a heart and its pericardium to perform a medical procedure on the heart, the method comprising the following steps:

(a) passing a guide catheter through a selected vein to establish a transvenous route to the right auricle of the heart;

(b) passing a leading guide wire through said guide catheter and into the right auricle so that a distal end of said leading guide wire is positioned against a wall of the right auricle;

(c) piercing said wall of the right auricle with said distal end of said leading guide wire;

(d) advancing said leading guide wire into the pericardial space; and (e) using said leading guide wire to perform a specific medical procedure on the heart.

28. The method of claim 27, wherein said step (c) of piercing said wall of the right auricle is performed without attaching a distal end of said guide catheter to said wall of the right auricle.

29. The method of claim 28, wherein said step (c) of piercing comprises the step of:

applying an axial force to a proximal end of said leading guide wire until said distal end of said leading guide wire pierces said wall of the right auricle.

* * * * *

UNITED STATES PATENT AND TRADEMARK OFFICE
CERTIFICATE OF CORRECTION

PATENT NO. : 6,200,303 B1
DATED : March 13, 2001
INVENTOR(S) : Richard L. Verrier et al.

It is certified that error appears in the above-identified patent and that said Letters Patent is hereby corrected as shown below:

<u>Title page,</u>
Item [75], Inventor, in the Inventor information, please replace "Verrior" with
-- Verrier --

Signed and Sealed this

Fourth Day of June, 2002

Attest:

Attesting Officer

JAMES E. ROGAN
*Director of the United States Patent and Trademark Office*